United States Patent
Ohta et al.

(10) Patent No.: US 11,427,520 B2
(45) Date of Patent: Aug. 30, 2022

(54) METHOD FOR PRODUCING TETRAFLUOROETHYLENE AND/OR HEXAFLUOROPROPYLENE

(71) Applicant: DAIKIN INDUSTRIES, LTD., Osaka (JP)

(72) Inventors: Toshihiko Ohta, Osaka (JP); Hideki Nakaya, Osaka (JP); Mai Hirai, Osaka (JP); Takashi Yasuhara, Osaka (JP); Atsushi Noguchi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/099,098

(22) Filed: Nov. 16, 2020

(65) Prior Publication Data

US 2021/0070679 A1    Mar. 11, 2021

Related U.S. Application Data

(63) Continuation of application No. PCT/JP2019/019722, filed on May 17, 2019.

(30) Foreign Application Priority Data

May 18, 2018  (JP) .............................. JP2018-096506

(51) Int. Cl.
| | | |
|---|---|---|
| *C07C 17/361* | (2006.01) | |
| *C07C 17/367* | (2006.01) | |
| *C07C 21/185* | (2006.01) | |
| *C07C 21/18* | (2006.01) | |
| *B01J 19/00* | (2006.01) | |

(52) U.S. Cl.
CPC .......... *C07C 17/361* (2013.01); *B01J 19/0093* (2013.01); *C07C 21/185* (2013.01); *B01J 2219/00033* (2013.01); *C07C 17/367* (2013.01)

(58) Field of Classification Search
CPC ............................ C07C 17/361; C07C 17/367
See application file for complete search history.

(56) References Cited

U.S. PATENT DOCUMENTS

| | | | |
|---|---|---|---|
| 2,709,182 | A  | 5/1955  | Farlow |
| 6,624,337 | B1 | 9/2003  | Manzer et al. |
| 2004/0112758 | A1 | 6/2004 | Bauer et al. |
| 2005/0240067 | A1 | 10/2005 | Bauer et al. |

(Continued)

FOREIGN PATENT DOCUMENTS

| | | |
|---|---|---|
| EP | 0 455 399 A2 | 11/1991 |
| GB | 766324 A | 1/1957 |
| JP | 4-228588 A | 8/1992 |

(Continued)

OTHER PUBLICATIONS

Mierdel, K. et al. "Energy and Resource Efficient Production of Fluoroalkenes in High Temperature Microreactors" ChemEngineering 2019, 3, 77; Published Sep. 24, 2019 (Year: 2019).*

(Continued)

*Primary Examiner* — Medhanit W Bahta
(74) *Attorney, Agent, or Firm* — Sughrue Mion, PLLC

(57) ABSTRACT

A process for producing one or both of tetrafluoroethylene and hexafluoropropylene, which includes pyrolyzing a low molecular weight fluorine compound by continuous reaction in a microreactor.

1 Claim, 1 Drawing Sheet

(56) References Cited

U.S. PATENT DOCUMENTS

2011/0184214 A1\* 7/2011 Hintzer .................. C07C 21/18
570/136

FOREIGN PATENT DOCUMENTS

| JP | 2003-501552 A | 1/2003 |
| JP | 2006-509831 A | 3/2006 |
| JP | 2016-013994 A | 1/2016 |
| WO | 2016/002632 A1 | 1/2016 |

OTHER PUBLICATIONS

English translation of WO2016/002632A1, Jan. 7, 2016, pp. 1-8 (Year: 2016).\*
Fairburn, J. A. et al. "Ultrapyrolysis of n-hexadecane in a novel micro-reactor" Fuel, 1990, vol. 69, pp. 1537-1545 (Year: 1990).\*
International Preliminary Report on Patentability (with translation of the Written Opinion) dated Dec. 3, 2020, issued by the International Bureau in application No. PCT/JP2019/019722.
Charlotte Wiles et al., "Recent advances in micro reaction technology", Chemical Communications, 2011, pp. 6512-6535, vol. 47, No. 23, ISSN 1359-7345.
Kenichi Kanno et al., "Microreactor: New Device for Organic and Enzymatic Synthesis", Yuki Gosei Kagaku Kyokaishi, 2002, pp. 701-707, vol. 60, No. 7, ISSN 0037-9980.
International Search Report for PCT/JP2019/019722, dated Aug. 6, 2019.
Extended European Search Report dated Jan. 25, 2022 by European Patent Office in counterpart European Application No. 19803443.1.

\* cited by examiner

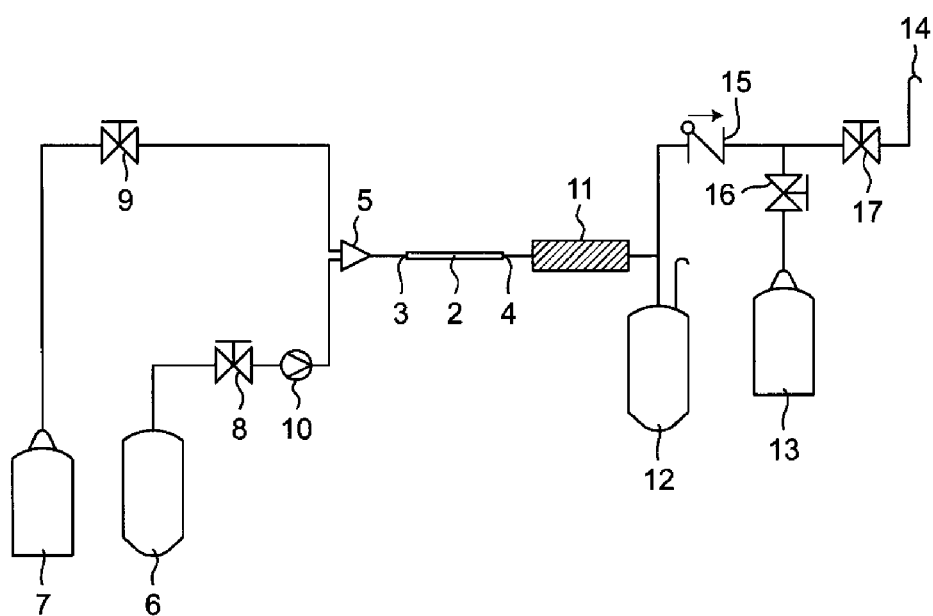

METHOD FOR PRODUCING TETRAFLUOROETHYLENE AND/OR HEXAFLUOROPROPYLENE

This is a continuation application under 37 C.F.R. § 1.53(b) of PCT/JP2019/019722 filed May 17, 2019, which claims priority from Japanese Patent Application No. 2018-096506 filed May 18, 2018, incorporated herein by reference in its entirety.

TECHNICAL FIELD

The present disclosure relates to a process for producing tetrafluoroethylene and/or hexafluoropropylene.

BACKGROUND ART

The pyrolysis of a perfluoroalkane is known as a method for producing tetrafluoroethylene and hexafluoropropylene (Patent Literature 1). In Patent Literature 1, a perfluoroalkane was added to a cylindrical container, heated and pyrolyzed to obtain tetrafluoroethylene and hexafluoropropylene.

CITATION LIST

Patent Literature

Patent Literature 1: Japanese Patent Laid-Open No. 2016-13994

SUMMARY OF THE INVENTION

Problem to be Solved by the Invention

The method of Patent Literature 1 has a problem that the conversion ratio and the selection ratio from a perfluoroalkane to tetrafluoroethylene and hexafluoropropylene were low. An object of the present disclosure is to provide a process for producing tetrafluoroethylene and/or hexafluoropropylene by pyrolysis at a high conversion ratio and a high selection ratio.

Means to Solve the Problem

The present disclosure includes the following aspects.
1. A process for producing tetrafluoroethylene and/or hexafluoropropylene, comprising:
pyrolyzing a low molecular weight fluorine compound by continuous reaction in a microreactor.
2. The process according to aspect 1, wherein the low molecular weight fluorine compound has a carbon chain having 4 to 28 carbon atoms.
3. The process according to aspect 1 or 2, wherein the low molecular weight fluorine compound has a carbon chain having 4 to 18 carbon atoms.
4. The process according to any one of aspects 1 to 3, wherein the low molecular weight fluorine compound is a perfluoroalkene.
5. The process according to any one of aspects 1 to 4, wherein the pyrolysis is performed in the temperature range of 620° C. to 720° C.
6. The process according to any one of aspects 1 to 5, wherein a diameter of the microreactor is 1 mm to 20 mm.
7. The process according to any one of aspects 1 to 6, wherein the pyrolysis is performed in the condition of mixing the low molecular weight fluorine compound and an inert gas.

Effect of the Invention

According to the present disclosure, a process for producing tetrafluoroethylene and/or hexafluoropropylene by pyrolysis at a high conversion ratio and a high selection ratio can be provided.

BRIEF DESCRIPTION OF DRAWING

The FIGURE shows an example of a microreactor system for implementing a method of the present disclosure.

EMBODIMENTS TO CARRY OUT THE INVENTION

In the present disclosure, a low molecular weight fluorine compound is pyrolyzed to produce tetrafluoroethylene and/or hexafluoropropylene.

As long as the above-mentioned low molecular weight fluorine compound is a low molecular weight fluorine compound having a carbon chain having 4 or more carbon atoms, the low molecular weight fluorine compound is not limited. The low molecular weight fluorine compound is a fluorine compound having a carbon chain having preferably 4 to 28 carbon atoms, more preferably 4 to 18 carbon atoms. For example, the low molecular weight fluorine compound may be linear or branched. For example, the above-mentioned carbon chain may be saturated or unsaturated. The above-mentioned low molecular weight fluorine compound may be used alone or as a mixture of two or more. Since liquid needs to be fed in a fixed amount with a pump or by pressure to pyrolyze these compounds, in the case of one low molecular weight fluorine compound, the low molecular weight fluorine compound is preferably a liquid at normal temperature. In the case of two or more low molecular weight fluorine compounds, the combination wherein the low molecular weight fluorine compounds which can be liquefied by mixing is preferable.

In one embodiment, the boiling point of the above-mentioned low molecular weight fluorine compound is preferably in the range of 100° C. to 500° C., and more preferably in the range of 150° C. to 400° C. at normal pressure.

In one embodiment, the above-mentioned low molecular weight fluorine compound preferably has low viscosity. For example, the viscosity of the above-mentioned low molecular weight fluorine compound is preferably 100 cP or less, and more preferably 50 cP or less.

In one embodiment, the above-mentioned low molecular weight fluorine compound does not contain a highly polar functional group which causes electric intermolecular interaction. Examples of such high polar functional groups include a hydroxyl group.

In one embodiment, the above-mentioned low molecular weight fluorine compound contains no oxygen atom. Using the low molecular weight fluorine compound containing no oxygen atom improves the selectivity of reaction in pyrolysis.

In a preferable embodiment, as long as the above-mentioned low molecular weight fluorine compound is a low molecular weight fluorine compound which has a boiling point in the range of 100° C. to 500° C. at normal pressure and has a carbon chain containing no oxygen atom and having 4 or more carbon atoms, the above-mentioned low molecular weight fluorine compound is not limited. The low molecular weight fluorine compound can be a fluorine compound having a carbon chain having preferably 4 to 28 carbon atoms, more preferably 4 to 18 carbon atoms.

Although the above-mentioned low molecular weight fluorine compound is not limited, the low molecular weight fluorine compound can be a fluoroalkane, a fluoroalkene or a fluoroalkyne having 4 or more carbon atoms, preferably 4 to 28 carbon atoms, more preferably 4 to 18 carbon atoms, more preferably 6 to 10 carbon atoms; or a derivative thereof.

The above-mentioned low molecular weight fluorine compound may be an oligomer of a fluorohydrocarbon having 2 to 4 carbon atoms, or preferably an oligomer of either or both of tetrafluoroethylene and hexafluoropropylene.

The above-mentioned "derivative" may be a compound in which a functional group is bound to a fluoroalkyl group, a fluoroalkenyl group or a fluoroalkynyl group.

The above-mentioned functional group may be an amino group (—$NH_2$), an imino group (=NH), an azo group (—N=N—), a diazo group (—$N^+$=N), an azido group (—$N_3$), a phenyl group containing no oxygen, or a salt thereof.

Examples of the above-mentioned salt include metallic salts, ammonium salts and organic amine salts. Examples of the metallic salts include salts of alkali metals such as sodium and potassium; and salts of alkaline-earth metals such as calcium and magnesium. Examples of the organic amine salts include salts of alkylamines such as methylamine and n-butylamine.

In one embodiment, the above-mentioned low molecular weight fluorine compound may be a perfluorocompound, namely a perfluoroalkane, a perfluoroalkene or a perfluoroalkyne.

In one embodiment, the above-mentioned low molecular weight fluorine compound may be a fluoroalkene having 4 to 28 carbon atoms, preferably 4 to 18 carbon atoms, more preferably 6 to 10 carbon atoms. In such an embodiment, the low molecular weight fluorine compound may be a perfluoroalkene which is linear, branched or partially or wholly cyclized. In a preferred embodiment, the low molecular weight fluorine compound may be perfluorooctene which is linear, branched or partially or wholly cyclized or perfluorodecylethylene which is linear, branched or partially or wholly cyclized.

The pyrolysis of the present disclosure is performed in continuous reaction. The pyrolysis of the present disclosure is typically performed in a microreactor.

In one embodiment, the low molecular weight fluorine compound is pyrolyzed as a mixture of the low molecular weight fluorine compound and an inert gas in a reactor. Using the inert gas enables flexibly controlling the linear velocity in the microreactor from not only the amount of the low molecular weight fluorine compound fed but also the amount of the inert gas fed and enables controlling decomposition behavior more flexibly.

Examples of the above-mentioned inert gas include nitrogen and noble gases (such as helium, neon and argon; preferably helium and argon). The above-mentioned inert gas is preferably nitrogen.

The flow rate of the low molecular weight fluorine compound introduced into the microreactor may be preferably 0.5 to 1.5 g/minute, and more preferably 0.6 to 1.0 g/minute.

When the inert gas is used, the flow rate of the inert gas introduced into the microreactor may be preferably 0.05 to 3.0 L/minute, and more preferably 0.3 to 1.5 L/minute in terms of the state at normal temperature (25° C.) and normal pressure (1 atm).

When the inert gas is used, the volume ratio of the low molecular weight fluorine compound introduced into the microreactor to the inert gas (low molecular weight fluorine compound/inert gas ratio) is not limited. The volume ratio may be, for example, 1 to 700, preferably 5 to 100, and more preferably 10 to 25.

The linear velocity of the low molecular weight fluorine compound or the mixture of the low molecular weight fluorine compound and the inert gas in the microreactor may be, for example, 5 to 1,500 mm/minute, preferably 50 to 1,000 mm/minute, and, for example, 75 to 750 mm/minute.

As long as the pyrolysis of the low molecular weight fluorine compound proceeds, the temperature in a microreactor is not limited. The temperature may be, for example, 620° C. or more, and preferably 650° C. or more, and can be 720° C. or less, and preferably 700° C. or less. Adjusting the temperature in the microreactor to 620° C. or more enables pyrolyzing the low molecular weight fluorine compound more certainly. Adjusting the temperature in the microreactor to 720° C. or less enables further suppressing the production of a by-product. In one embodiment, the temperature in a microreactor can be 620° C. to 720° C., and preferably 650° C. to 700° C.

As long as the pyrolysis of the low molecular weight fluorine compound proceeds, the pressure in a microreactor is not limited. The pressure may be, for example, 800 to 1,200 Pa, and preferably 950 to 1,100 MPa.

In one embodiment, the temperature in a microreactor is 620° C. to 720° C., and preferably 650° C. to 700° C., and the pressure in the microreactor may be 800 to 1,200 Pa, and preferably 950 to 1,100 MPa.

In one embodiment, a process of the present disclosure may include a step of cooling a product obtained after a step of pyrolyzing the low molecular weight fluorine compound.

At the time of the above-mentioned cooling, the product is preferably cooled in a microreactor to stop side reaction, suppress the decomposition of the product and improve the selection ratio by rapid cooling.

Although the diameter (or channel width) and the length of a microreactor for cooling are not limited, and, for example, may be the same as the microreactor used in the pyrolysis step, a longer microreactor is preferable. For example, the diameter (or channel width) of the microreactor for cooling can be preferably 20 mm or less, more preferably 10 mm or less, and further preferably 6 mm or less, and can be preferably 1 μm or more, more preferably 100 μm or more, further preferably 1 mm or more, and further more preferably mm or more. The length of the microreactor may be preferably 20 cm or more, more preferably 100 cm or more, and further preferably 300 cm or more.

As long as the above-mentioned cooling temperature is higher than the melting point of the product, the above-mentioned cooling temperature is not limited. For example, when the product is tetrafluoroethylene (melting point −120° C., normal boiling point −80° C.), the cooling temperature may be −80° C. to −120° C., and preferably −95 to −105° C. in the case of normal pressure. When the product is hexafluoropropylene (melting point −153° C., normal boiling point −28° C.), the cooling temperature may be −28° C. to −153° C., preferably −30 to −140° C., and more preferable −40 to −70° C. When the product is a mixture of tetrafluoroethylene and hexafluoropropylene, the cooling steps can also be separated by adjusting the cooling temperature to −40 to −70° C. in the former step and the cooling temperature to −95 to −105° C. in the latter step. The unreacted raw material can also be collected by providing a cooler and adjusting the cooling temperature to 10 to 0° C. further previously to the former step.

A usual cooling method can be used for a cooling method, the product can be cooled, for example, by immersing the microreactor in an ice bath; various organic solvent baths (−20 to −80° C.) such as dry ice/ethanol; a liquid nitrogen bath (boiling point −196° C.); or the like.

In the process of the present disclosure, the low molecular weight fluorine compound is pyrolyzed to obtain at least one of tetrafluoroethylene and hexafluoropropylene.

In the pyrolysis, perfluorooctene which is linear, branched or partially or wholly cyclized or perfluorodecylethylene which is linear, branched or partially or wholly cyclized is pyrolyzed into tetrafluoroethylene in a low temperature region in an early stage of pyrolysis and tetrafluoroethylene further is pyrolyzed in a high temperature region, and is bound to tetrafluoroethylene to produce hexafluoropropylene.

In the present disclosure, the above-mentioned "microreactor" means a reactor used for continuous reaction and having a significantly smaller length in the width direction than in the fluid flow direction.

The above-mentioned microreactor is used in a reaction method in which the raw material is reacted continuously with the volume of the reactor reduced as compared with a reaction method called a batch in a chemical reaction process. Using the microreactor enables controlling the temperature of the reaction system at a high speed subtly, suppressing the decomposition of the product and the side reaction, and improving the yield.

The diameter (or channel width) of the above-mentioned microreactor may be preferably 20 mm or less, more preferably 10 mm or less, and further preferably 6 mm or less. Reducing the channel width enables removing heat more efficiently and controlling the temperature strictly. Moreover, reducing the channel width enables suppressing rapid reaction or the decomposition of a reactant (for example, tetrafluoroethylene) in the reactor. The diameter (or channel width) of the above-mentioned microreactor may be preferably 1 μm or more, more preferably 100 μm or more, further preferably 1 mm or more, and further more preferably mm or more. Increasing the channel width enables increasing the throughput. In one embodiment, the diameter (or channel width) of the microreactor may be 1 μm or more and 20 mm or less, preferably 1 mm or more and 20 mm or less, more preferably 1 mm or more and 10 mm or less, and further preferably 2 mm or more and 6 mm or less. The channel width means the shortest distance between the opposite wall surfaces of the channel.

The length of the above-mentioned microreactor may be preferably 20 cm or more, more preferably 30 cm or more, and further preferably 40 cm or more. The length of the above-mentioned microreactor may be preferably 200 cm or less, more preferably 100 cm or less, and further preferably 60 cm or less. In one embodiment, the length of the microreactor may be 20 cm or more and 200 cm or less, preferably 30 cm or more and 100 cm or less, more preferably 30 cm or more and 60 cm or less. When the reaction temperature, the feeding ratio and the like are constant, lengthening the microreactor enables the extension of the practical reaction time, and the conversion ratio is expected to improve. Shortening the microreactor enables shortening the practical reaction time, and the selection ratio is expected to improve.

In one embodiment, the above-mentioned microreactor is incorporated into a system as shown in the FIGURE (hereinafter also called a "microreactor system").

As shown in the FIGURE, in the above-mentioned microreactor system, the inlet side 3 of a microreactor 2 is connected with a raw material tank 6 and an inert gas tank 7 through a collision mixing part 5. Valves 8 and 9 are provided between the microreactor 2 and the respective tanks 6 and 7. Moreover, a pump 10 for conveying a raw material from the raw material tank 6 to the microreactor 2 is provided between the microreactor 2 and the raw material tank 6. A low molecular weight fluorine compound conveyed from the raw material tank 6 is mixed with an inert gas in the collision mixing part 5. When the low molecular weight fluorine compound is a liquid, the low molecular weight fluorine compound can be gasified in the collision mixing part 5. The mixture is conveyed to the microreactor 2 and pyrolyzed.

In the above-mentioned microreactor system, the outlet side 4 of the microreactor 2 is connected with a cooler 11. The mixture after pyrolysis is cooled in the cooler 11. The cooler 11 is further connected with a liquid sample container 12, a gas sample container 13 and an open vent 14. Valves 16 and 17 are provided between the cooler 11 and the gas sample container 13 and between the cooler 11 and the open vent 14, respectively. A check valve 15 is provided on the exhaustion side of the liquid sample container 12. A component which is cooled and becomes a liquid are collected in the liquid sample container 12, and a component which remains gas are collected in the gas sample container 13.

According to the process of the present disclosure, the low molecular weight fluorine compound can be pyrolyzed into at least one of tetrafluoroethylene and hexafluoropropylene at a high conversion ratio and a high selection ratio. According to the process of the present disclosure, the low molecular weight fluorine compound can be pyrolyzed without using a solvent. Therefore, it is easy to obtain the target tetrafluoroethylene and hexafluoropropylene from the reaction mixture after pyrolysis.

EXAMPLES

Examples 1-1, 1-2 and 1-3 (Reaction Temperature 670° C.)

As a pyrolysis reactor, a microreactor for pyrolysis having an inner diameter of 6.35 mm and a length of 40 cm was used. The inlet side of this microreactor was connected with a tank of perfluorooctene (raw materials A) or perfluorodecylethylene (raw materials B) as a raw material and a nitrogen gas tank through a collision mixing part. The outlet side of the microreactor was connected with a microreactor for cooling having an inner diameter of 3.18 mm and a length of 4 m. The temperature in the microreactor for pyrolysis was raised to 670° C. The microreactor for cooling was cooled with ice (0° C.)

A raw material containing perfluorooctene and/or perfluorodecylethylene at a ratio shown in the following Table 1 was fed at 0.25 g/minute, and nitrogen was fed at 0.5 L/minute from the tanks to the microreactor. In the microreactor, the raw material was pyrolyzed to obtain a reaction product containing tetrafluoroethylene (TFE) and hexafluoropropylene (HFP).

Evaluation

The reaction product obtained above was analyzed by GC/MS. The following Table 1 shows the results.

Examples 2-1 and 2-2 (Reaction Temperature 720° C.)

Tetrafluoroethylene and hexafluoropropylene were obtained in the same way as in the above-mentioned Example 1-1 except that the reaction temperature was changed to 720° C., and a raw material shown in the following Table 1 was used. The obtained reaction product was analyzed by GC/MS. The following Table 1 shows the results.

Examples 3-1 and 3-2 (Gas Supply Rate 1.5 L/Minute)

Tetrafluoroethylene and hexafluoropropylene were obtained in the same way as in Example 1-1 and Example 2-2 except that the gas supply rate of nitrogen was adjusted to 1.5 L/minute. The obtained reaction product was analyzed by GC/MS. The following Table 1 shows the results.

Comparative Example 1

An autoclave having a capacity of 5 cc was charged with 1.65 g (1 ml) of perfluorooctene, and the upper air was replaced with nitrogen. The perfluorooctene was heated to 670° C., maintained for 20 minutes and then cooled to normal temperature. The autoclave was then opened, and the internal product was analyzed by GC/MS, so that the conversion ratio was 98%, and tetrafluoroethylene and hexafluoropropylene could not, however, be detected.

TABLE 1

| Example | Raw material A Parts by mass | Raw material B Parts by mass | Air supply rate L/minute | Conversion ratio % | TEE selection ratio % | HEP selection ratio % |
| --- | --- | --- | --- | --- | --- | --- |
| 1-1 | 100 |  | 0.5 | 84 | 65 | 20 |
| 1-2 |  | 100 | 0.5 | 77 | 59 | 14 |
| 1-3 | 50 | 50 | 0.5 | 77 | 62 | 19 |
| 2-1 | 100 |  | 0.5 | 89 | 35 | 71 |
| 2-2 |  | 100 | 0.5 | 84 | 42 | 62 |
| 3-1 | 100 |  | 1.5 | 75 | 84 | 6 |
| 3-2 |  | 100 | 1.5 | 82 | 17 | 69 |

INDUSTRIAL APPLICABILITY

According to the present disclosure, tetrafluoroethylene and hexafluoropropylene can be obtained by pyrolysis.

The invention claimed is:

1. A process for producing at least one of tetrafluoroethylene and hexafluoropropylene, comprising: pyrolyzing perfluorooctene or a mixture of perfluorooctene and an inert gas by continuous reaction in a microreactor, wherein the pyrolysis is performed in the temperature range of 620° C. to 720° C., a linear velocity of perfluorooctene or the mixture is 5 to 1,500 mm/minute in the microreactor, and the microreactor has a diameter of 1 mm to 20 mm and a length of 20 cm or more.

* * * * *